(12) United States Patent
Hashimoto et al.

(10) Patent No.: US 6,641,584 B2
(45) Date of Patent: Nov. 4, 2003

(54) HOOK CABLE FOR FIXING ATLANTOAXIAL JOINT AND SYSTEM FOR FIXING THE SAME

(75) Inventors: Tomoyuki Hashimoto, Hokkaido (JP); Kazuya Oribe, Tokyo (JP); Futoshi Miyaura, Tokyo (JP); Noriyuki Ina, Aichi-ken (JP)

(73) Assignee: Showa Ika Kohgyo Co., Ltd., Nagoya (JP)

( * ) Notice: Subject to any disclaimer, the term of this patent is extended or adjusted under 35 U.S.C. 154(b) by 73 days.

(21) Appl. No.: 09/955,942

(22) Filed: Sep. 20, 2001

(65) Prior Publication Data

US 2002/0040222 A1 Apr. 4, 2002

(30) Foreign Application Priority Data

Sep. 22, 2000 (JP) ........................................ 2000-289289

(51) Int. Cl.7 ............................................. A61B 17/56
(52) U.S. Cl. ....................................................... 606/61
(58) Field of Search ............................... 606/61, 72, 73, 606/65, 53, 70

(56) References Cited

U.S. PATENT DOCUMENTS

| 4,047,523 A | * | 9/1977 | Hall ............................ 606/61 |
|---|---|---|---|
| 4,635,953 A | * | 1/1987 | Robertson et al. .......... 280/480 |
| 4,974,992 A | * | 12/1990 | Harter .......................... 404/25 |
| 5,306,275 A | * | 4/1994 | Bryan .......................... 606/61 |
| 5,395,370 A | | 3/1995 | Müller et al. |
| 5,395,371 A | * | 3/1995 | Miller et al. .................. 606/61 |
| 5,498,262 A | | 3/1996 | Bryan |
| 5,520,689 A | | 5/1996 | Schläpfer et al. |
| 5,653,708 A | * | 8/1997 | Howland ...................... 606/61 |
| 5,676,084 A | * | 10/1997 | Palmer et al. ............ 114/230.2 |
| 5,725,527 A | * | 3/1998 | Biedermann et al. ......... 606/61 |
| 5,725,582 A | * | 3/1998 | Bevan et al. ................. 606/61 |
| 5,810,817 A | * | 9/1998 | Roussouly et al. ........... 606/61 |
| 5,947,965 A | | 9/1999 | Bryan |
| 6,077,262 A | | 6/2000 | Schläpfer et al. |
| 6,077,263 A | | 6/2000 | Ameil et al. |

FOREIGN PATENT DOCUMENTS

| EP | 743045 | | 11/1996 | | |
|---|---|---|---|---|---|
| WO | WO 95/06440 | * | 3/1995 | ................. | 606/61 |
| WO | WO 98/41160 | * | 9/1998 | ................. | 606/61 |

\* cited by examiner

Primary Examiner—Pedro Philogene
(74) Attorney, Agent, or Firm—Greenblum & Bernstein, P.L.C.

(57) ABSTRACT

Hook cable including a hook for hooking to an arcus posterior in an atlanto. A cable which can freely bend is integrally provided in a base portion of the hook.

6 Claims, 4 Drawing Sheets

HOOK CABLE FOR FIXING ATLANTOAXIAL JOINT AND SYSTEM FOR FIXING THE SAME

BACKGROUND OF THE INVENTION

1. Field of the Invention

The present invention relates to a hook cable used for a fixing method with respect to an atlantoaxial joint unstable symptom between a first cervical vertebra (an atlanto) and a second cervical vertebra (an epistropheus), and a system for fixing the same.

2. Description of Related Art

As a method of fixing an atlantoaxial joint between an atlanto (a first cervical vertebra) 1 and an epistropheus (a second cervical vertebra) 3, for example, as shown in FIGS. 1A and 1B, there is executed a method of obliquely screwing and inserting a pair of right and left screws 9 to lateral roots 7 of the atlanto 1 from an inferior articular process 5 of the epistropheus 3, aligning right and left autologous bones 15 between an arcus posterior 11 of the atlanto 1 and an arcus vertebrae 13 of the epistropheus 3, and fastening the arcus posterior 11 and the arcus vertebrae 13 by a titanium wire 17.

As described above, in the related art, since it is necessary to wind the titanium wire 17 around the arcus posterior 11 of the atlanto 1 and the arcus vertebrae 13 of the epistropheus 3, it is hard to perform the winding operation, and since it is necessary to pay attention so as to prevent such as a bone resection loss or a breakage of the titanium wire 17 from being generated at a time of fastening the titanium wire 17, there is a problem that it is necessary to pay attention to the fastening operation.

SUMMARY OF THE INVENTION

The present invention is made by taking the problem as described above into consideration. According to a first aspect of the present invention, there is provided a hook cable provided with a hook for hooking to an arcus posterior in an atlanto, wherein a cable which can freely bend is integrally provided in a base portion of the hook.

In the hook cable as described in the first aspect, the structure is made such that the hook is provided with a projection on a surface hooked to the arcus posterior.

According to a third aspect of the present invention, there is provided a system for fixing an atlantoaxial joint, in which a screw hole is provided in a head portion of a screw freely inserting to an atlanto from an epistropheus, an engagement groove communicated with the screw hole is provided, a cable provided in a hook freely hooked to an arcus posterior in the atlanto is provided so as to be freely engaged with the engagement groove, and a fixing screw freely fixing the cable engaged with the engagement groove is provided so as to be freely meshed with the screw hole. The structure is made such that a screw portion is provided in an inserting direction of the screw, and a guide hole is provided in an axial core of the screw.

DETAILED DESCRIPTION OF THE PREFERRED EMBODIMENT

Figure 1A:
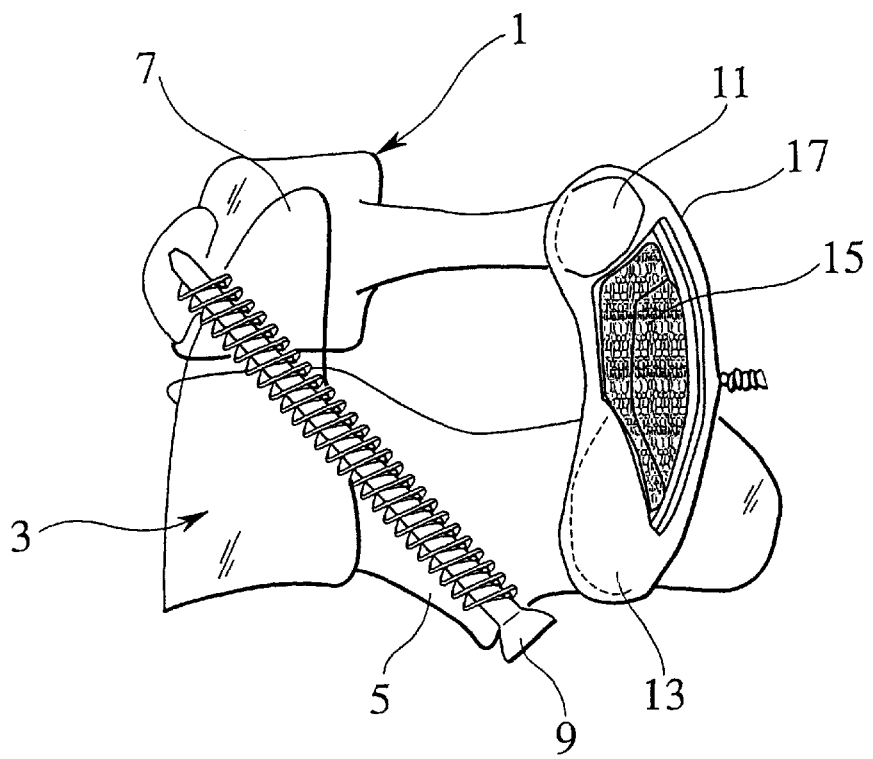
FIGS. 1A and 1B are explanation views of a related embodiment.
Figure 1B:
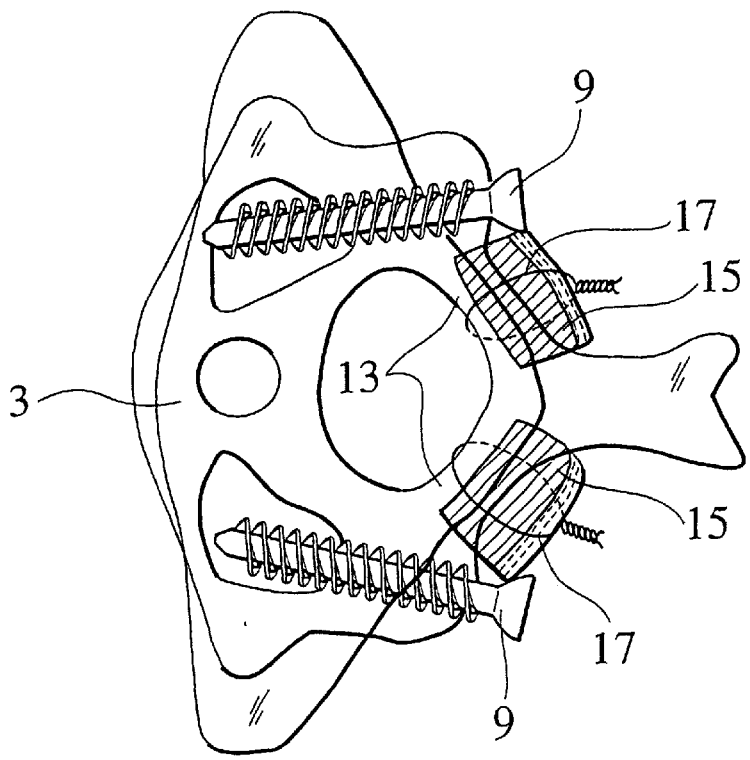

Hereinafter, a description an embodiment will be given with reference to the accompanying drawings. However, the same reference numerals are attached to the same elements as those of the above related structure, and an overlapping description will be omitted.

Figure 2:
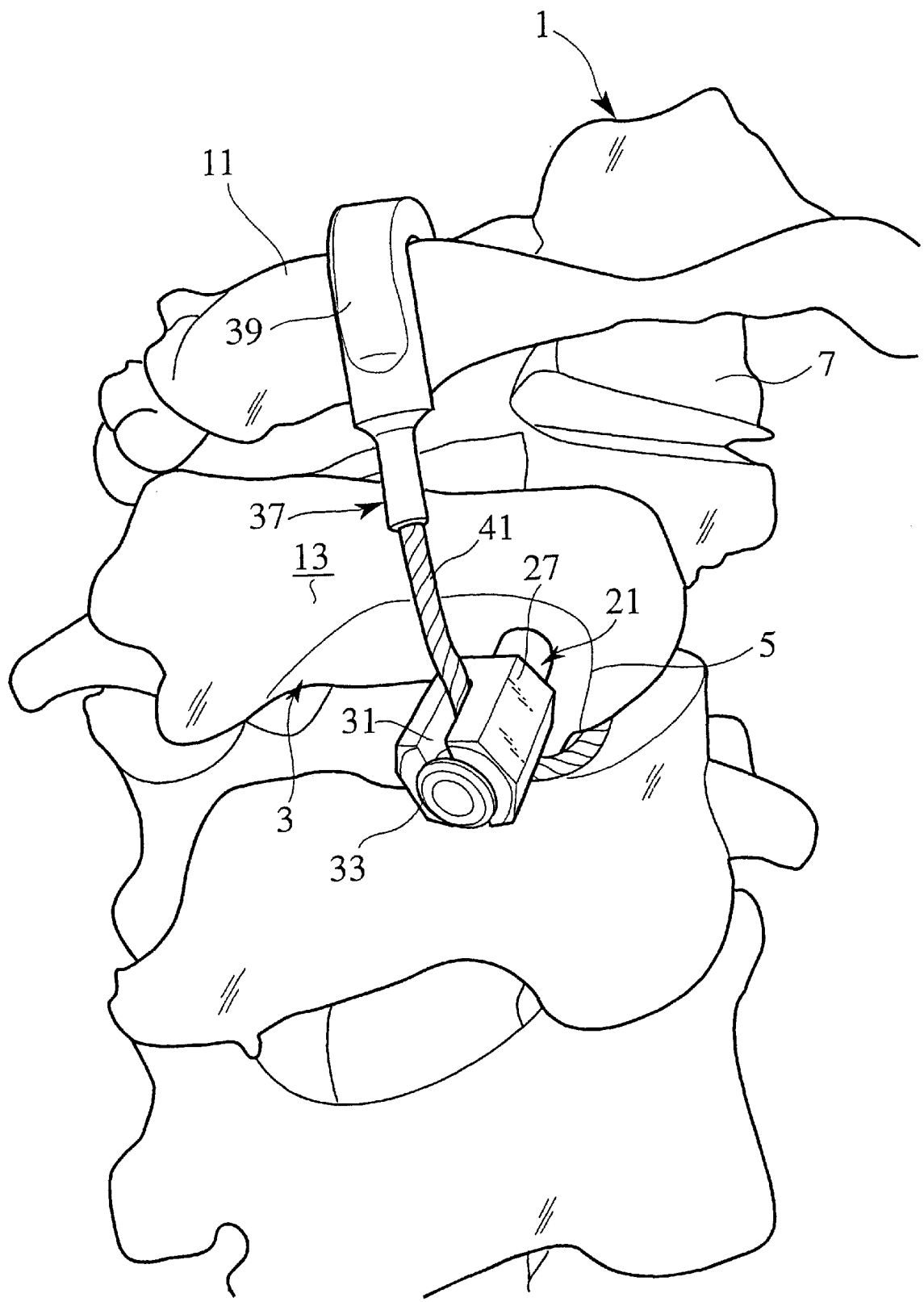
FIG. 2 is a explanation view showing a used example of a hook cable according to an embodiment of the present invention and a fixing screw thereof.

With reference to FIG. 2, a screw 21 used for a method of fixing an atlantoaxial joint between an atlanto 1 and an epistropheus 3 is obliquely screwed and inserted to an outer lateral root 7 of the atlanto 1 from an inferior articular process 5 of the epistropheus 3 in the same manner as above screw 9.

Figure 3:
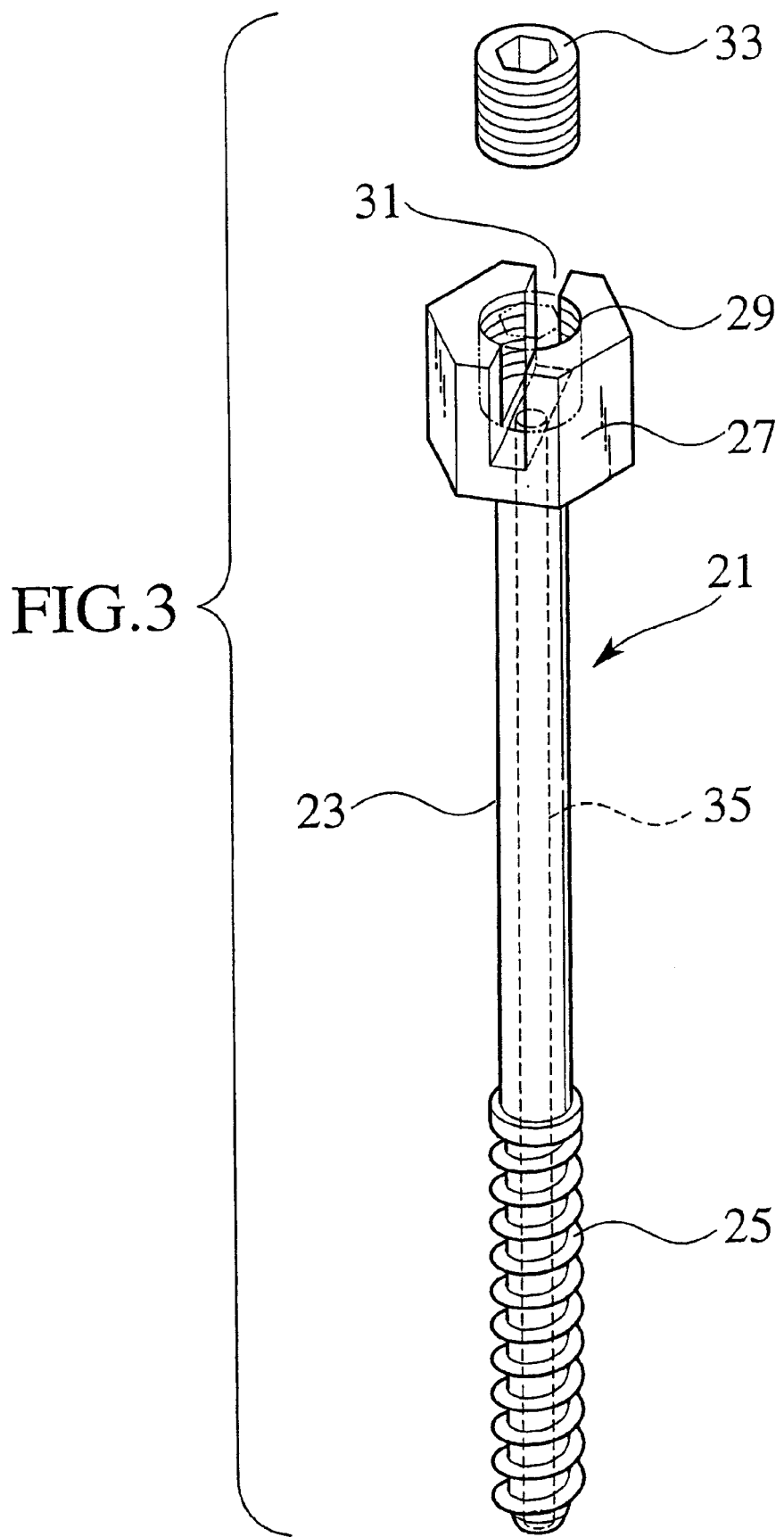
FIG. 3 is a perspective explanation view of a screw.

The above screw 21 is provided with a screw portion 25 such as a tap in a front end side of a shaft body 23, as shown in FIG. 3, and is provided with a polygonal large diameter head portion 27 in a base end side of the shaft body 23. An axial screw hole 29 is formed in the head portion 27 and an engagement groove 31 communicated with the screw hole 29 is formed in a suitable direction, in the present embodiment, in an axial direction of the screw 21. Further, a fixing screw 33 freely engaging with and disengaging from the screw hole 29 is provided, and a guide hole 35 is provided so as to extend through an axial core of the shaft body 23.

Figure 4:
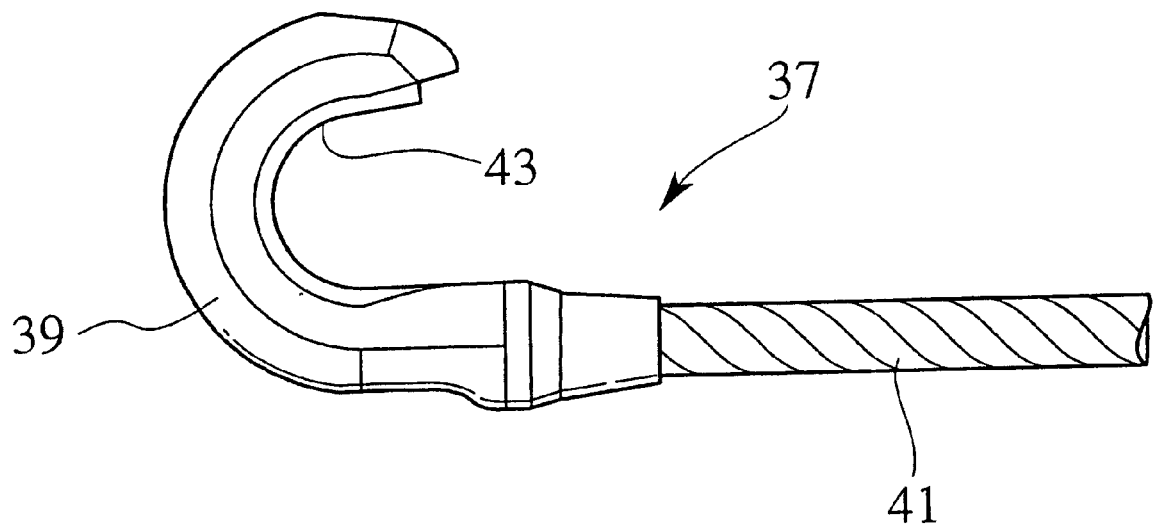
FIG. 4 is a explanation view of a hook cable.

A hook cable 37 freely engaged with and fixed to an arcus posterior 11 of the atlanto 1 is provided with a hook 39 formed in a circular arc shape, as shown in FIG. 4, and a cable 41 which can freely bend and has a suitable length freely engaged with and disengaged from the engagement groove 31 formed in the head portion of the screw 21 is integrally connected to a base portion of the hook 39. Further, a projection portion 43 is formed on a surface where the hook 39 is hooked with the arcus posterior 11. The projection portion 43 has a function slightly eating into the arcus posterior 11, and in the present embodiment, is formed as one protrusion which slightly protrudes.

In the structure as described above, in order to screw and insert the screw 21, at first, a screw hole having a small diameter is obliquely formed in the outer lateral root 7 of the atlanto 1 from the inferior articular process 5 of the epistropheus 3 by a drilling tool such as an air drill or, thereafter inserting into the guide hole 35 of the screw 21, and the screw 21 is screwed and inserted to the screw hole while using a guide wire inserted to the screw hole as a guide.

Thereafter, by hooking the hook 39 in the hook cable 37 to the arcus posterior 11 of the atlanto 1, engaging the cable 41 with the engagement groove 31 formed in the head portion 27 of the screw 21 so as to suitably tension, and engaging the fixing screw 33 with the screw hole 29 so as to fasten and fix the cable 41, the joint is fixed between the atlanto 1 and the epistropheus 3.

When hooking the hook 39 of the hook cable 37 to the arcus posterior 11 of the atlanto 1 in the manner as described above, the projection portion 43 is formed on the surface where the hook 39 is hooked to the arcus posterior 11, so that the projection portion 43 eats into the arcus posterior 11, whereby it is possible to securely hook at a predetermined position. At this time, since it is unnecessary to wind up the cable 41 or the like inside the arcus posterior 11 in the atlanto 1 and the arcus vertebrae 13 in the epistropheus 3, a fixing operation can be easily and safely executed in comparison with the related method as described above.

The present disclosure relates to subject matter contained in priority Japanese Patent Application No. 2000-289289, filed on Sep. 22, 2000, the contents of which is herein expressly incorporated by reference in its entirety.

What is claimed is:

1. A hook cable comprising:
   a circular arc-shaped hook extending from a base portion;
   the circular arc-shaped hook comprising a projection arranged on a surface and being configured to hook to an arcus posterior in an atlanto; and
   a cable which can freely bend extending from the base portion of the circular arc-shaped hook,
   wherein the base portion completely surrounds a portion of the cable, and
   wherein the cable is integrally connected to the base portion.

2. A hook cable according to claim 1, wherein the projection is formed in one protruding groove.

3. A system for fixing an atlantoaxial joint comprising:
   a screw capable of being freely inserted into an atlanto from an epistropheus;
   a head portion arranged at an end portion of the screw;
   a screw hole provided in the head portion;
   an engagement groove communicated with the screw hole;
   a cable comprising a circular arc-shaped hook that includes a projection, wherein the circular arc-shaped hook is configured to hook into an arcus posterior on an atlanto, and wherein the cable engages with the engagement groove; and
   a fixing screw threaded into the screw hole and being capable of freely fixing the cable with respect to the engagement groove.

4. A system for fixing an atlantoaxial joint according to claim 3, wherein the head portion is polygonal, and wherein the screw further comprises a shaft body integrally connected to the head portion, and a screw portion provided at a front end in an inserting direction of the shaft body.

5. A system for fixing an atlantoaxial joint according to claim 4, wherein the screw further comprises a guide hole that extends through an axial core of the shaft body.

6. A system for fixing an atlantoaxial joint comprising:
   a screw comprising external threads configured to be inserted into an atlanto from an epistropheus, a head portion arranged an opposite end, an internally threaded hole arranged in the head portion, and an engagement groove extending from one side of the head portion to another side of the head portion and communicating with the internally threaded hole;
   a cable having a first end configured to be received in the engagement groove and a second end;
   an arc-shaped hook connected to the second end of the cable and comprising a projection formed on an inner curved surface of the arc-shaped hook, wherein the arc-shaped hook is configured to hook into an arcus posterior on an atlanto; and
   a fixing screw threaded into the internally threaded hole and being capable of fixing the cable to the screw.

\* \* \* \* \*